United States Patent
Bourier et al.

(10) Patent No.: US 9,147,289 B2
(45) Date of Patent: Sep. 29, 2015

(54) METHOD FOR VISUALIZING THE QUALITY OF AN ABLATION PROCESS

(71) Applicant: SIEMENS AKTIENGESELLSCHAFT, Munich (DE)

(72) Inventors: Felix Bourier, Lappersdorf (DE); Alexander Benjamin Brost, Erlangen (DE); Andreas Kleinoeder, Erlangen (DE); Klaus Kurzidim, Regensburg (DE); Norbert Strobel, Heroldsbach (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 402 days.

(21) Appl. No.: 13/626,277

(22) Filed: Sep. 25, 2012

(65) Prior Publication Data

US 2013/0169624 A1 Jul. 4, 2013

(30) Foreign Application Priority Data

Sep. 27, 2011 (DE) .......................... 10 2011 083 522

(51) Int. Cl.
| | |
|---|---|
| G06T 15/00 | (2011.01) |
| G06T 19/00 | (2011.01) |
| A61B 18/02 | (2006.01) |
| A61B 19/00 | (2006.01) |
| A61B 18/14 | (2006.01) |
| A61B 18/00 | (2006.01) |

(52) U.S. Cl.
CPC ................ *G06T 19/00* (2013.01); *A61B 18/02* (2013.01); *A61B 19/50* (2013.01); *A61B 18/1492* (2013.01); *A61B 2018/0022* (2013.01); *A61B 2018/00357* (2013.01); *A61B 2018/00375* (2013.01); *A61B 2018/0212* (2013.01); *A61B 2019/504* (2013.01); *A61B 2019/505* (2013.01); *A61B 2019/5238* (2013.01)

(58) Field of Classification Search
None
See application file for complete search history.

(56) References Cited

U.S. PATENT DOCUMENTS

| | | | | |
|---|---|---|---|---|
| 2003/0181809 A1* | 9/2003 | Hall et al. | ...................... | 600/425 |
| 2007/0189457 A1* | 8/2007 | Deinzer | ...................... | 378/98.12 |
| 2007/0268287 A1* | 11/2007 | Magnin et al. | ................. | 345/419 |
| 2008/0071173 A1* | 3/2008 | Aldrich | .......................... | 600/439 |
| 2009/0306643 A1* | 12/2009 | Pappone et al. | ................. | 606/33 |
| 2010/0020161 A1* | 1/2010 | Bertrams et al. | ................. | 348/51 |

(Continued)

FOREIGN PATENT DOCUMENTS

| | | | |
|---|---|---|---|
| DE | 102005045363 A1 | | 4/2007 |
| WO | WO 2010140069 A1 | * | 12/2010 |

*Primary Examiner* — Aaron M Richer
*Assistant Examiner* — Anh-Tuan V Nguyen

(57) ABSTRACT

A method for visualizing the quality of an ablation process with a processing and display unit is provided. A 3D dataset of an anatomical object and a 3D image model of an ablation instrument are provided, wherein the 3D image model models at least the surface of the ablation instrument. A position and an alignment of the 3D image model of the ablation instrument within the anatomical object is specified, wherein the 3D image model of the ablation instrument is incorporated into the 3D dataset of the anatomical object. At least a part of the incorporated 3D image model of the ablation instrument and of the 3D dataset of the anatomical object is presented and at least one characteristic quality value is determined as a function of the location of the 3D image model of the ablation instrument in relation to the anatomical object.

17 Claims, 8 Drawing Sheets

(56) References Cited

U.S. PATENT DOCUMENTS

| | | | |
|---|---|---|---|
| 2010/0020926 A1* | 1/2010 | Boese et al. | 378/44 |
| 2010/0040766 A1* | 2/2010 | Chappa et al. | 427/2.3 |
| 2010/0049099 A1* | 2/2010 | Thapliyal et al. | 601/2 |
| 2010/0063496 A1* | 3/2010 | Trovato et al. | 606/34 |
| 2010/0268223 A1* | 10/2010 | Coe et al. | 606/41 |
| 2011/0082451 A1* | 4/2011 | Melsky | 606/14 |

* cited by examiner

METHOD FOR VISUALIZING THE QUALITY OF AN ABLATION PROCESS

CROSS REFERENCE TO RELATED APPLICATIONS

This application claims priority of German Patent Application No. 10 2011 083 522.9 DE filed Sep. 27, 2011. All of the applications are incorporated by reference herein in their entirety.

FIELD OF INVENTION

A method for planning and visualizing the quality of an ablation process is provided. Further, a corresponding apparatus for planning and visualizing the quality of an ablation process is provided.

BACKGROUND OF INVENTION

A condition that is becoming increasingly significant in medicine and epidemiologically and is affecting an ever greater proportion of the population, currently some 4%, is atrial fibrillation. In patients suffering from atrial fibrillation, disruptive pulses originating from the lung veins (pulmonary veins) pass into the cardiac conduction system of the heart, causing the patient's heart to beat only irregularly or very rapidly. A usual method of interventional therapy of atrial fibrillation is the electrical isolation of the lung veins. Catheters are introduced into the left atrium and the tissue in the area of the pulmonary veins, from which the disruptive signals originate, is ablated. This ablation is on the one hand attempted with conventional radio-frequency catheters (RF catheters). RF catheters make small punctilinear lesions (appr. 4 mm×4 mm). Isolating pulmonary veins with this technique over a large-surface area necessitates many working steps and a large amount of time. A new development in the area of catheter technology is so-called single-shot devices which are able, because of their larger size to ablate large areas of tissue in a single application. A preferred case involves what is known as a cryoballoon, as is offered for example under the name Arctic Front Cryoballoon®, by Medtronic CryoCath, PointeClaire, Quebec, Canada, which is placed in the area of the lung veins to be ablated and then cooled to a temperature of around −40° to −50° Celsius. Further examples for single-shot devices are the laser balloon, e.g. from CardioFocus, Marlborough, Mass., USA, or the PVAC multi-electrode catheter from Medtronic Ablation Frontiers, Carlsbad, Calif., USA. The now withdrawn "High-Intensity Focused Ultrasound (HIFU)" catheter of Pro-Rhythm, Inc., Ronkonkoma, N.Y., USA also falls into the category of single-shot devices.

A prerequisite for successful use of single-shot devices, such as the cryoballoon for example, is generally good contact between catheter surface and heart tissue, since only in this way may energy, e.g. in the form of heat or cold, be transmitted in a sufficient quantity and the tissue ablated thereby, i.e. explicitly permanently destroyed. Devices must additionally often be placed in a precisely defined anatomical area to make effective and safe ablation possible. The cryoballoon must for example be placed in the antrum of the left atrium. Energy emissions in the incorrect areas are not effective and even dangerous, e.g. when they occur within a pulmonary vein. The anatomical configuration of the lung veins and of the left atrium is complex to an especially great extent and inter-individually very variable, so that single-shot devices such as cryoballoons for example cannot be used for each patient with a sufficiently accurate fit. If single-shot devices can be used with an accurate fit this as a rule brings about a very much faster and safer isolation of the lung veins by comparison with use of an RF catheter.

A decisive question before beginning the procedure is whether a single-shot device, e.g. a cryoballoon, can be used or whether there must be recourse to a conventional RF catheter. Clinical practice shows for example that a cryoballoon can achieve a very good ablation with non-selective patient quality in 25% of cases; in 75% of cases a supplementary ablation with RF catheters must take place after the cryoprocedure.

A widely-used method is to be presented here by way of example for use of a cryoballoon as a single-shot device for pulmonary vein isolation in the left atrium. In other single-shot devices the method is generally similar. With device-dependent details there can however be deviations. Currently for use of a cryoballoon a decision is made before the beginning of the procedure about the possibility of using it based on 3D imaging acquired beforehand. The suitable balloon diameter is determined with available 3D data by means of dimensioning in the slice images of these preoperative datasets. Under some circumstances this is also undertaken in a 3D view of a segmented left atrium. If only a two-dimensional measurement is to be able to be undertaken, there is the danger of inaccuracies. The measurement of all conceivable balloon positions in the antrum area of all four lung veins would be associated with a disproportionately high time outlay.

Whether the choice of balloon size was correct and whether it could be correctly placed can be checked in fluoroscopy by means of contrast means injection or Doppler ultrasound. Laser balloons which are equipped with an endoscope allow an optical check as to whether they are in good contact or not. These examples show that the check can however as a rule not take place until during the interventional procedure. If the choice of ablation instrument was not optimal however or if the ablation instrument could not be correctly placed, further measures which can impose strain on the patient and mean additional outlay in terms of time and money are necessary.

SUMMARY OF INVENTION

An object is to provide a method for improving the choice and use of an ablation instrument compared to the previous method of operation.

The object is achieved with a method for visualizing the quality of an ablation process and an apparatus for visualizing the quality of an ablation process according to the independent claims.

The basic idea is a method for visualizing the quality of an ablation process with a processing and display means. The method comprises the following:

S1) Provision of a 3D dataset of at least one anatomical object of an object to be examined;

S2) Provision of at least one 3D image model of an ablation instrument, wherein the 3D image model models at least the surface of the ablation instrument;

S3) Specification of at least one position and an alignment of the 3D image model of the ablation instrument within the at least one anatomical object;

S4) Incorporation of the 3D image model of the ablation instrument into the 3D dataset of the at least one anatomical object;

S5) Presentation of at least a part of the incorporated 3D image model of the ablation instrument and of the 3D dataset of the at least one anatomical object;

S6) Determination of at least one characteristic quality value as a function of the location of the 3D image model of the ablation instrument in relation to the at least one anatomical object.

Since successful use of single-shot devices depends on how accurately these may be inserted into the anatomy of the patient and placed in the left atrium, the provided method, which may be executed with a processing and display means, e.g. a computer with screen, supports a doctor for example in the initial planning phase in the choice of an ablation instrument and in the placing of said instrument. If a doctor is able to assess the quality of an ablation process, he is put into a position to be able to evaluate different ablation positions and plan the process in this way.

In the first method step, a 3D dataset of at least one anatomical object of an object to be examined is provided. The datasets may be provided for example by acquisition, e.g. with the aid of an imaging apparatus, by accepting information from such an apparatus or in general by loading it into a memory of the processing and display means. The object to be examined, the patient, may be a human being or an animal. A spatial image may be obtained by computed tomography (CT), magnetic resonance tomography (MR) or another spatial imaging method. A further option consists of using an x-ray device. Through a suitable series of x-ray images from different directions around the patient a spatial image may be computed. A 3D dataset featuring at least one anatomical object may be computed from this spatial image, with the aid of a segmentation algorithm for example. Segmentation is a widely-used method in medical image processing. In this context, the method may be understood as the separation of the anatomical object from surrounding tissue, bone and other image components not belonging to the anatomical object. The anatomical object is for example an organ or a vessel which is to come into contact with an ablation instrument.

In the next method step, at least one 3D image model of an ablation instrument, wherein at least the surface of the ablation instrument is modeled, is provided. A 3D image model of the ablation instrument may for example be obtained from a file or from a database, of the manufacturer for example, or is determined on the basis of technical drawings or measurements, e.g. by 3D scanning. In the use of cryoballoons for pulmonary vein isolation, there are currently suitable balloon models with a variable diameter, e.g. 23 mm or 28 mm for instance.

In the third method step, at least one position and at least one alignment of the 3D image model of the ablation instrument within the at least one anatomical object is specified or provided. This may principally be done manually by an input instrument, e.g. at the processing and display means, which for example displays the 3D dataset of the area under examination on a screen, or position and alignment are predetermined by an algorithm.

In the next method step, the 3D image model of the ablation instrument is incorporated at the correct location into the 3D dataset of the at least one anatomical object. Incorporation at the correct location means that the 3D image model of the ablation instrument is incorporated at the position provided and with the alignment provided within the 3D dataset of the area under examination. The ablation instrument will to all intents and purposes be placed virtually in the examination area.

In the next method step, at least a part of the incorporated 3D image model of the ablation instrument and of the 3D dataset of the at least one anatomical object is displayed on a monitor for example.

In the sixth method step, at least one characteristic quality value is determined depending on the position of the 3D image model of the ablation instrument relative to the at least one anatomical object. Since the location, i.e. the position and the alignment, of the 3D image model of the ablation instrument in relation to the anatomical object is known and furthermore the coordinates of the surface of the ablation instrument may also be computed, e.g. from digital image processing algorithms, as to the extent to which the surface of the ablation instrument is in contact with the inner wall of a vessel for example. A possible characteristic quality value is thus for example a percentage which specifies the ratio of surface in contact to surface not in contact. Further characteristic quality values are for example for each point on the surface of the 3D image model of the ablation instrument, the assignment of the value "1" if the corresponding point rests on the inner wall of the anatomical object, otherwise the value "0". It is also possible in this case to take into account the deformation of the anatomy and of the ablation instrument.

The at least one characteristic quality value is visualized during the presentation of the at least one part of the incorporated 3D image model of the ablation instrument and of the 3D dataset of the at least one anatomical object. In the case of the last example, the points with the value "1" may be shown white for example, the points with the value "0" may be shown black. This means that the points at which the surface of the 3D image model of the ablation instrument rests against the inner wall of the anatomical object may easily be recognized.

A further method step may be executed after the sixth method step:

S7) Checking an abort criterion, especially the activation of a pushbutton, and on non-fulfillment of the abort criterion, jumping to method step S3).

An abort criterion, e.g. whether a pushbutton or a switch is activated, is thus checked. If the abort criterion is fulfilled the method is ended, otherwise the method continues with the third method step, the provision of a position and an alignment of the 3D image model of the ablation instrument within the anatomical object, whereby a repeatable loop and thus an iterative method is produced.

The 3D dataset of the at least one anatomical object includes at least one lung vein and the left atrium of the object to be examined. As described at the start, atrial fibrillation is caused by disruptive pulses from the pulmonary veins which merge into the cardiac conduction system of the heart. The ablation instrument is used for ablation in the area of the left atrium, so that it is expedient for this area to be present as a 3D dataset for the case in which treatment of atrial fibrillation is being planned.

The 3D dataset of the at least one anatomical object may include further information, especially information about a position of scar tissue, a wall thickness and/or a wall property, such as thermal conductivity value or modulus of elasticity. The anatomy model, as well as the actual anatomy, may also map further information, for example the presence of scar tissue, which provides data about the underlying electrical properties. A model that provides both the cellular composition and also the function of the anatomy shown is useful. On the basis of this information it is then possible to plan an individualized therapy.

In a further embodiment, the further information in the presentation of the at least one part of the incorporated 3D image model of the ablation instrument and of the 3D dataset of the at least one anatomical object is visualized. This makes it possible for the doctor to give a better assessment of whether a position of the ablation instrument is suitable, since tissue there may possibly already be scar tissue and therefore a further treatment would not be sensible.

In a further embodiment, the further information is included in the determination of the at least one characteristic quality value depending on the location of the 3D image model of the ablation instrument in relation to the at least one anatomical object. In the determination of the characteristic quality value "percentage of the ablation instrument surface in contact with the inside of an organ" scar tissue may be taken into account for example.

The ablation instrument may comprise a rotationally-symmetrical, especially a balloon-shaped, a pear-shaped or a rim-shaped object part. The axis of rotation of the rotationally-symmetrical object part also determines the alignment of the 3D image model of the ablation instrument and a determinable point of the 3D image model of the ablation instrument. The aim of single-shot devices is to ablate tissue over a large surface area in a single application. If these ablation instruments are used in tubular objects, such as vessels or at least partly cylindrical organs, a shape with a round cross-section, i.e. especially a spherical, pear or rim shape, is sensible. The axis of rotation or longitudinal axis of rotationally-symmetrical objects is sensible as a determination feature for the alignment of the 3D image model of the ablation instrument. With the establishment of a point of the 3D image model of the ablation instrument, the position of the 3D image model of the ablation instrument may be defined by specifying this point. For example the focus of the 3D image model of the ablation instrument or a point on the axis of rotation or a point on the circumference of the ablation instrument may be selected as position or location determination point.

At least one part of the axis of rotation of the rotationally-symmetrical object part may be marked, especially a part that represents a guide wire of the ablation instrument, in the 3D image model of the ablation instrument. Ablation instruments are frequently navigated in the vessel with the aid of a guide wire which is disposed as an extension of the axis of rotation or longitudinal axis on the ablation instrument. In planning the placement of single-shot devices it should be ensured that their alignment is also able to be realized. Only in this way is it guaranteed that a doctor may place the cryoballoon, for example by catheter manipulation, in a desired orientation. The marking of the location of the guide wire supplements the 3D image model of the ablation instrument by this component.

Single-shot devices also feature areas in which the most energy is emitted. These may be assigned a corresponding device geometry. With a cryoballoon in which most energy is emitted along the equator, it is sensible to assign the balloon an equator plane. An axis at right angles to the equator plane to which the central point of the balloon runs is sensible as an orientation. It corresponds to an axis through the two poles, the polar axis.

An energy emission profile of the ablation instrument, which assigns an energy emission value to each point of the ablation instrument, is included in the determination of the at least one characteristic quality value. The effect of single-shot devices of different forms of energy, e.g. laser balloons or cryoballoons, may be quantified and visualized, by that area of the single-shot device being considered through which energy is preferably emitted. The location of the highest energy emission is determined there. With a cryoballoon for example the most energy is emitted along the equator. Further energy emission areas or a quantitatively more precise determination of the energy emission by the device geometry may be defined by an energy emission profile. The energy emission profile indicates the energy emission changes as one moves away from the center.

An embodiment provides that the characteristic quality values may be energy emission values of each point of the ablation instrument on the at least one anatomical object. If the 3D image model of the ablation instrument is placed in the area under examination, the energy emission profile may be projected onto the surrounding grid network by plotting a surface through the preferred energy emission locations, such as the equator line with cryoballoons for example, which is then intersected with the grid network. After this surface intersects with the anatomy model, those grid points are known which experience the maximum energy input. Then the energy emission profile is transferred accordingly to the neighboring locations. Thus each point in the environment of the placed single-shot device is allocated a scalar value which describes the energy input at its point. These scalar values may also be visualized in order to illustrate the ablation effect of the single-shot device.

It is also conceivable for a further characteristic quality value to be the overall energy emission value which is determined by the sum of all characteristic quality values of the energy emission values of each point of the ablation instrument to the at least one anatomical object. I.e. all energy emission values which from the standpoint of the anatomical object are energy inputs are summed, and through this the overall energy input for a specific placing of a single-shot device is obtained. The energy input to the grid network structure may also be computed and visualized overall for a number of placements of one or more ablation instruments.

In a development of the method, with the aid of an optimization method, the position and that alignment of the 3D image model of the ablation instrument within the at least one anatomical object with the greatest overall energy emission value is determined. Optimization methods, such as the least squares method, Monte Carlo method etc., are widely-used methods in mathematics to minimize or maximize a target function. In the present case the overall energy emission value is the target function which is maximized by variation of the position and alignment of the 3D image model of the ablation instrument within the anatomical object. It is further conceivable to define the balloon catheter placement as a "constrained optimization problem". The optimization algorithm then determines all positions and alignments of the ablation instrument which guarantee that a pre-determinable overall energy input will be achieved. Another option is for the user to predetermine points, so-called desired ablation lines, and in an optimization method the method then places the 3D image model of the ablation instrument, e.g. a cryoballoon, so that its equator matches the desired ablation lines and the overall energy emission value is at its maximum.

In a further embodiment, at least one area within the at least one anatomical object is able to be predetermined and immediately after the third method step the provided position is set to a pre-determinable position or to the next position within the at least one pre-determinable area, if the provided position lies outside the at least one pre-determinable area. This feature makes it possible to define "forbidden areas", i.e. areas in which the ablation instrument may not be placed. This enables avoiding pushing the balloon too far into the pulmonary veins or two close to other, sensitive structures such as the feed pipes or the left auricle. If an attempt is made to place the 3D image model of the ablation instrument outside the pre-determinable area, the position is set to a pre-determinable "default" position, e.g. an origin position, or to the position which is at the smallest distance from the pre-determinable area.

The following further method steps may be executed after the sixth method step:

S6a) Provision of a 2D dataset which represents at least a part of the at least one anatomical object, especially a 2D dataset of a fluoroscopy.

S6b) In the 2D dataset, visualization of the position and the alignment of the 3D image model of the ablation instrument and/or visualization of the 3D image model of the ablation instrument, wherein especially a sectional plane of the 3D image model of the ablation instrument is visualized which corresponds to the projection plane of the 2D dataset.

S6c) Jump to method step S6a), if a second abort criterion, especially the actuation of the pushbutton, is not fulfilled.

If the desired ablation location has been determined for the isolation of each pulmonary vein, with the assistance of fluoroscopy overlaying techniques which are also known under the name of "augmented fluoroscopy", the doctor may be shown for example on a screen how far away an ablation instrument is from the desired ablation location. With precise modeling of the ablation instrument e.g. of a balloon catheter, it is likewise conceivable to show further details of this catheter, e.g. its tip, built-in markers etc., in the augmented fluoroscopy image. This may support the doctor in the positioning of the real catheter.

In a further embodiment, immediately after method step S6a), at least a part of the 3D dataset of the at least one anatomical object is registered with the 2D-dataset, especially non-rigid, and thereby an updated position and an updated alignment of the 3D image model of the ablation instrument is determined. Since the introduction of the balloon catheter may result in the deformation of the left atrium, such deformations are taken into account in the above-mentioned calculations. It is likewise conceivable that displacements occur during the introduction of the balloons. It is therefore expedient, using post-registration methods, to update the position and the alignment of the 3D image model of the ablation instrument, i.e. adapt it to the fluoroscopic image for example.

The second basic idea relates to an apparatus for visualizing the quality of an ablation process comprising at least one processing and display means, which is embodied to acquire a 3D dataset of at least one anatomical object of an object to be examined, to accept a 3D image model of an ablation instrument, wherein the 3D image model models at least the surface of the ablation instrument, to accept a position and an alignment of the 3D image model of the ablation instrument within the at least one anatomical object, to incorporate the 3D image model of the ablation instrument into the 3D dataset of the at least one anatomical object in the correct location, to present at least a part of the incorporated 3D image model of the ablation instrument and of the 3D dataset of the at least one anatomical object and to determine at least one characteristic quality value depending on the location of the 3D image model of the ablation instrument in relation to the at least one anatomical object.

The exemplary embodiments described in greater detail below represent preferred exemplary embodiments.

DETAILED DESCRIPTION OF INVENTION

Figure 1:
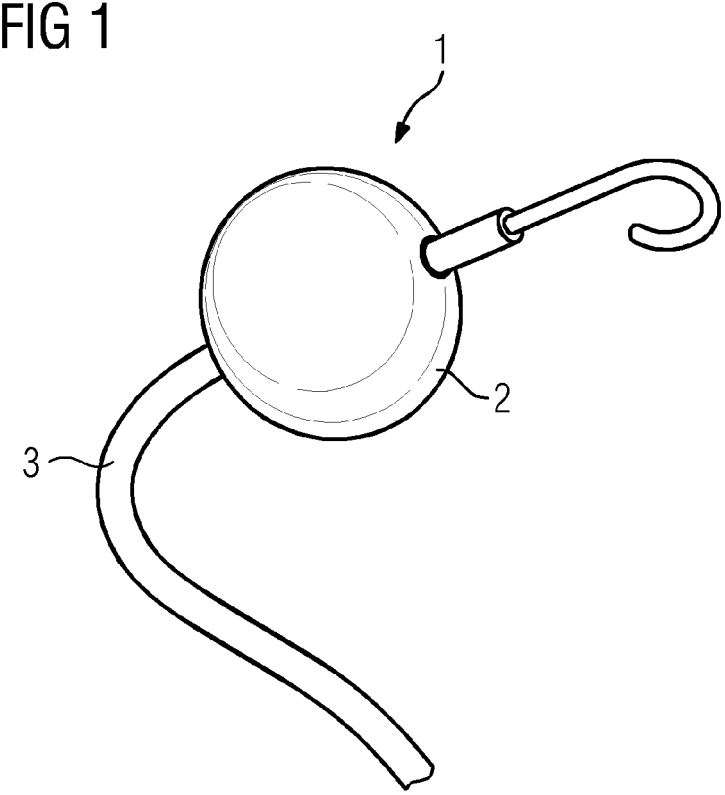
FIG. 1 shows an embodiment of a cryoballoon.

FIG. 1 shows a single-shot device 1 for carrying out an ablation in the form of a cryoballoon. Disposed at the end of a small tubular catheter 3 is an inflatable, spherical or balloon-shaped body 2, which may be cooled to a temperature of around −40° to −50° Celsius. On contact with tissue, said tissue freezes at the contact point and scar tissue is formed. Scar tissue possesses a low electrical conductivity, through which the passing on of undesired electrical pulses is interrupted.

Figure 2:
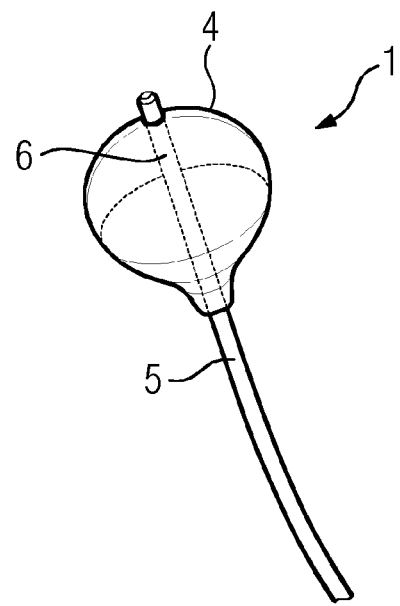
FIG. 2 shows an embodiment of a laser balloon.

FIG. 2 shows a single-shot device 1 for carrying out an ablation in the form of a laser balloon. Located inside the pear-shaped catheter part 4, which is disposed on a guide wire 5, is a laser 6, which heats up the surrounding tissue when activated, so that scar tissue is formed.

Figure 3:
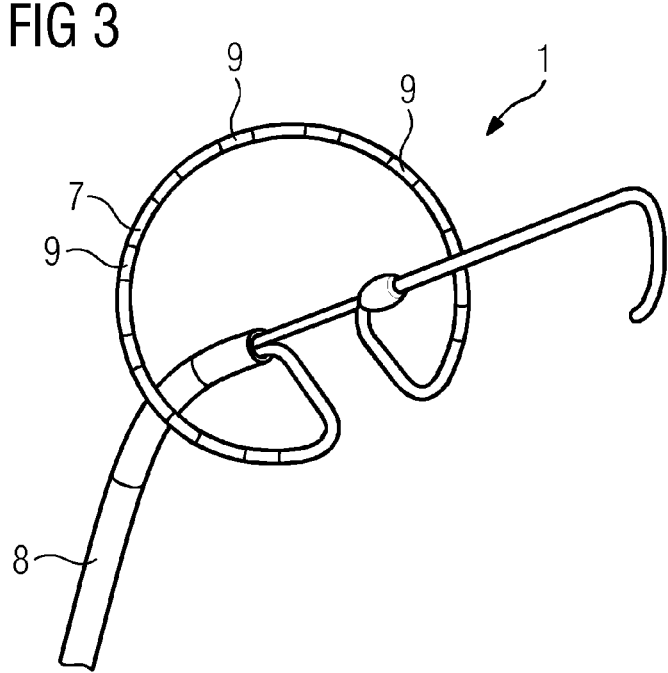
FIG. 3 shows an embodiment of a multi-electrode catheter.

FIG. 3 shows a single-shot device 1 for carrying out an ablation in the form of a multi-electrode catheter. Disposed beyond the circumference of an open rim-shaped or circular structure 7, which is disposed at the end of a guide wire 8, are a number of electrodes 9. The electrodes 9 provide local heating of tissue, hereby producing scar tissue.

Figure 4:
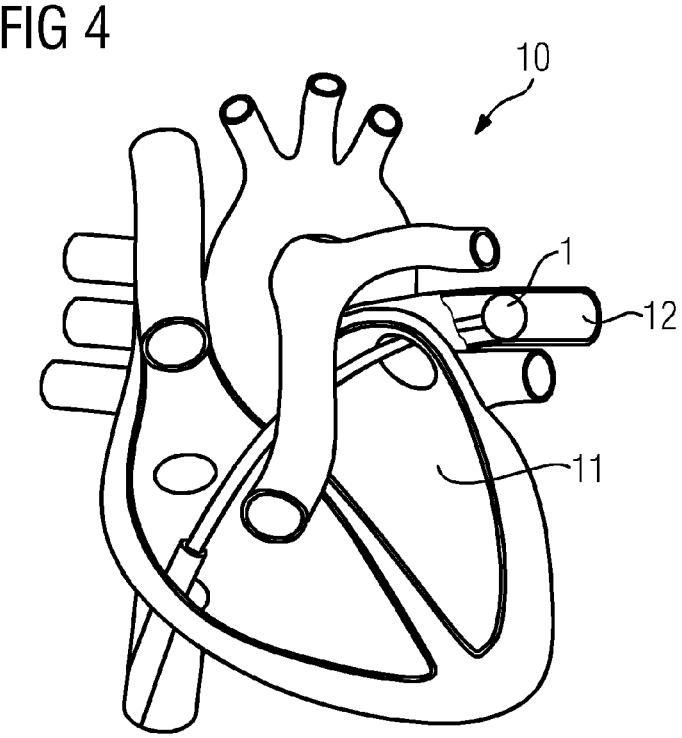
FIG. 4 shows a schematic diagram of an ablation procedure with a single-shot device.

Shown in FIG. 4 is a schematic diagram of an ablation procedure on a heart 10 with a single-shot device. The single-shot device 1 or the catheter is pushed from below via the inferior caval vein, the right atrium and the left atrium 11 into the outlet of the left upper pulmonary vein 12. The actual ablation process is carried out at a suitable point in which a circular scar zone is embodied through heat or cold, which prevents an electrical conductor of the pulses between lung veins and heart causing atrial fibrillation. Success in the use of single-shot devices depends on how accurate the fit is with which said devices are inserted into the anatomy of the patient and may be placed in a left atrium. Energy emissions in incorrect areas are not effective and are even dangerous, e.g. if they occur within a pulmonary vein.

Figure 5:
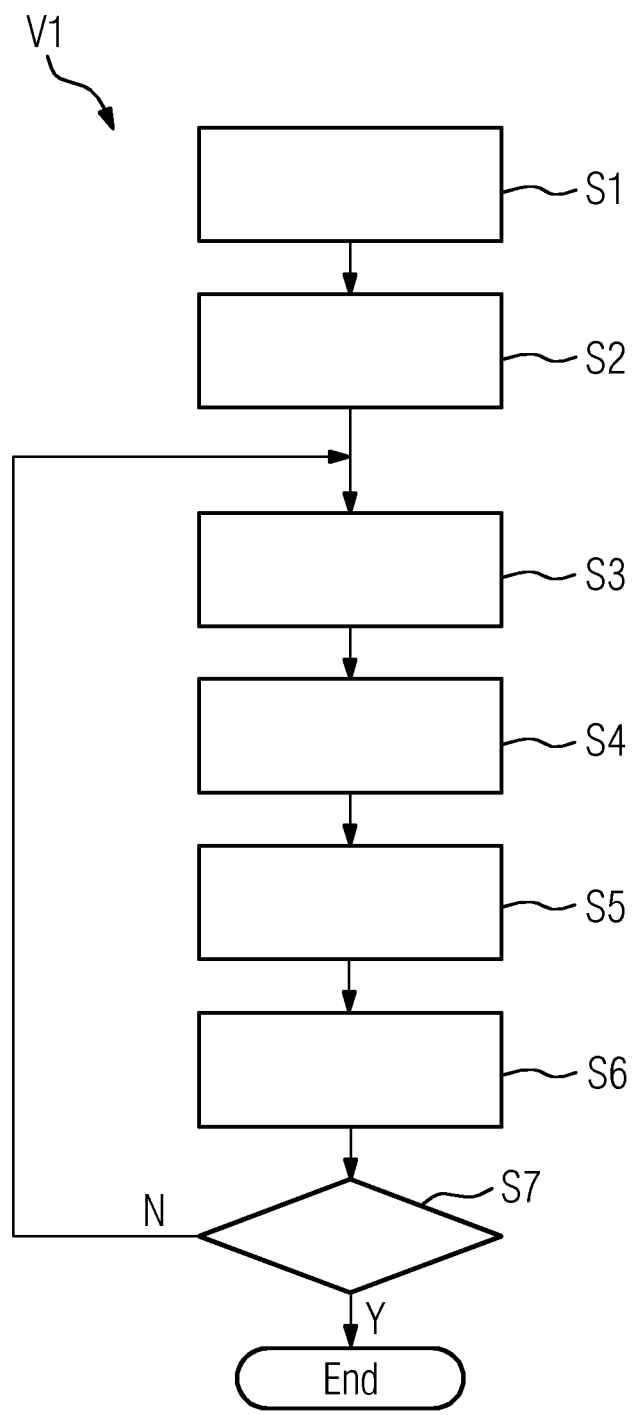
FIG. 5 shows a typical flow diagram of a first method.

FIG. 5 shows by way of example a flow diagram V1 of a method for visualizing the quality of an ablation process. The method includes the method steps S1 through S7. The individual method steps are as follows:

S1) Acquisition of a 3D dataset of at least one anatomical object of an object to be examined;

S2) Provision of a 3D image model of an ablation instrument, wherein the 3D image model models at least the surface of the ablation instrument;

S3) Provision of a position and an alignment of the 3D image model of the ablation instrument within the at least one anatomical object;

S4) Incorporation of the 3D image model of the ablation instrument into the 3D dataset of the at least one anatomical object at the correct location;

S5) Presentation of at least a part of the incorporation of the 3D image model of the ablation instrument and of the 3D dataset of the at least one anatomical object;

S6) Determination of at least one characteristic quality value as a function of the location of the 3D image model of the ablation instrument in relation to the at least one anatomical object.

S7) Checking an abort criterion, especially the activation of a pushbutton, and on non-fulfillment, "N" of the abort criterion, jumping to method step S3, otherwise, "Y", ending "End" the method.

Figure 6:
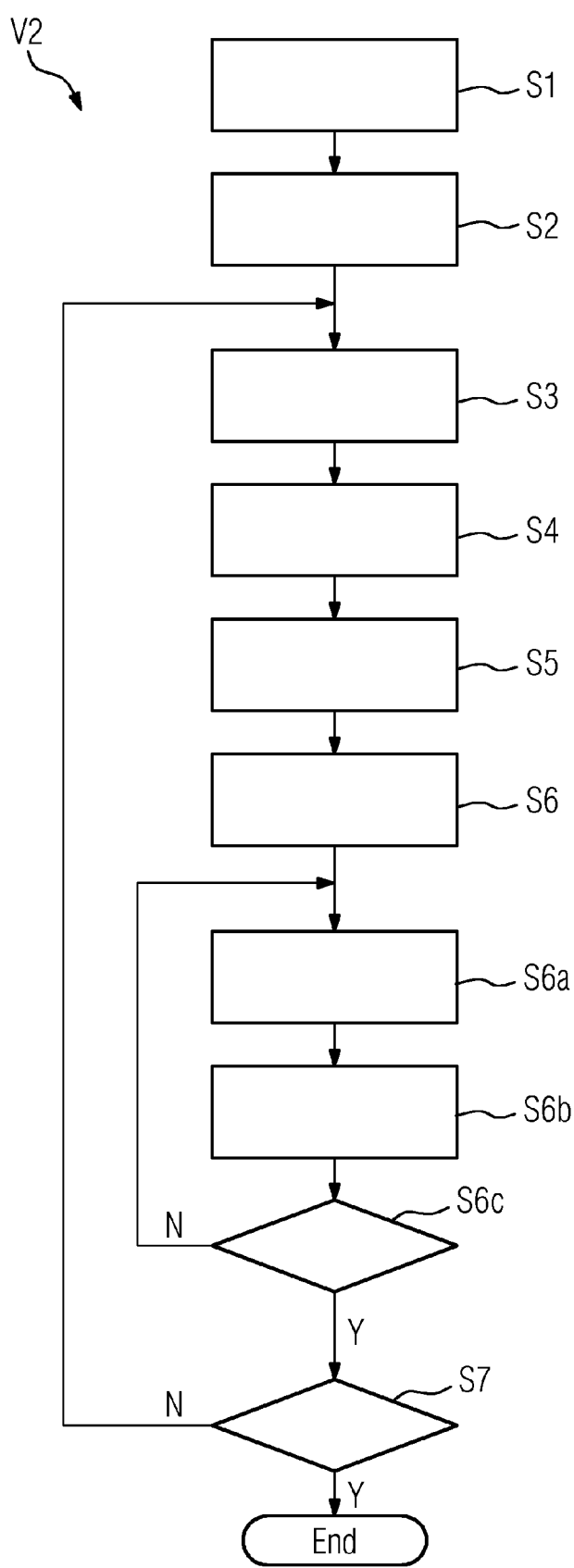
FIG. 6 shows a typical flow diagram of a second method.

FIG. 6 shows by way of example a flow diagram V2 of a second method for visualizing the quality of an ablation process. The method supplements the method depicted in FIG. 5 by the method steps S6a through S6c, which are inserted between method steps S6 and S7. The added method steps are as follows:

S6a) Provision of a 2D dataset which represents at least a part of the at least one anatomical object, especially a 2D dataset of a fluoroscopy;

S6b) In the 2D dataset, visualization of the position and the alignment of the 3D image model of the ablation instrument and/or visualization of the 3D image model of the ablation instrument, wherein especially a sectional plane of the 3D image model of the ablation instrument is visualized which corresponds to the projection plane of the 2D dataset;

S6c) Jump to method step S6a, if a second abort criterion, especially the actuation of the pushbutton, is not fulfilled, "N", otherwise, "Y", jump to method step S7.

Figure 7:
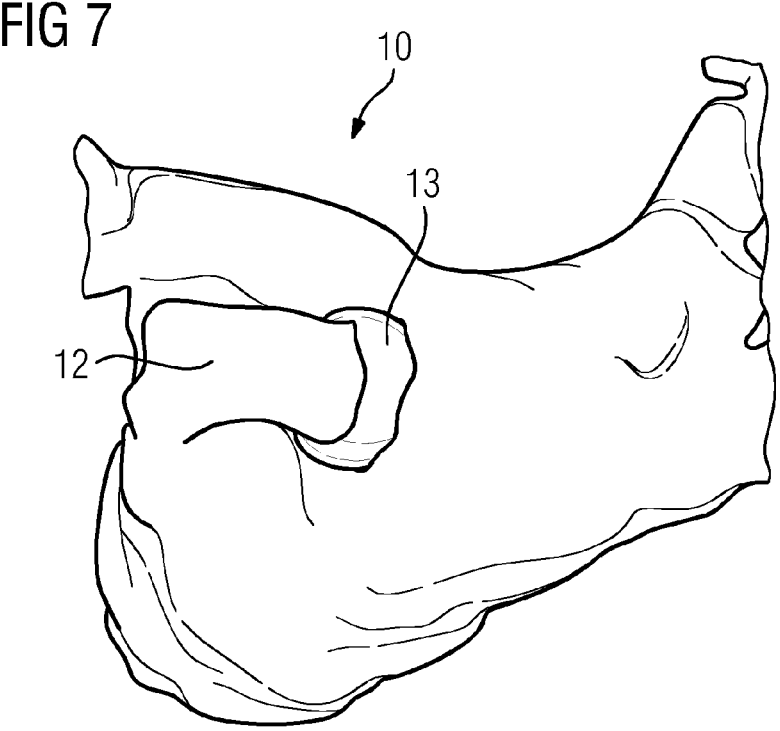
FIG. 7 shows an exemplary embodiment of the result of placement of a cryoballoon with a small diameter.

FIG. 7 shows an exemplary embodiment of the result of a placement of the cryoballoon 13 with a small, e.g. 23 mm, diameter. The cryoballoon 13 is placed on a pulmonary vein 12. Also shown is a part of the heart 10.

Figure 8:
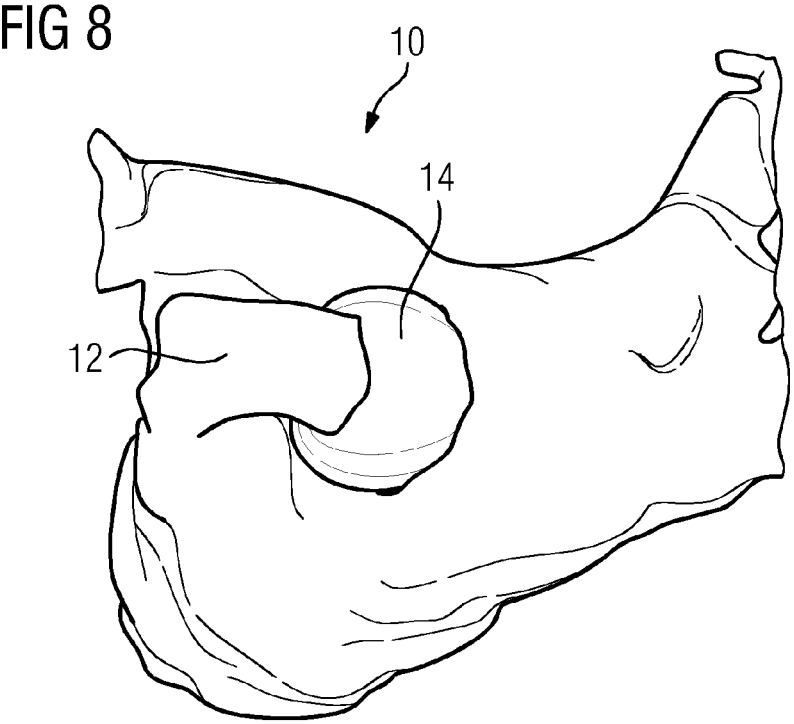
FIG. 8 shows an exemplary embodiment of the result of placement of a cryoballoon with a large diameter.

FIG. 8 shows an exemplary embodiment of the result of a placement of the cryoballoon 14 with a large diameter, e.g. a diameter of 28 mm, on a pulmonary vein 12.

Figure 9:
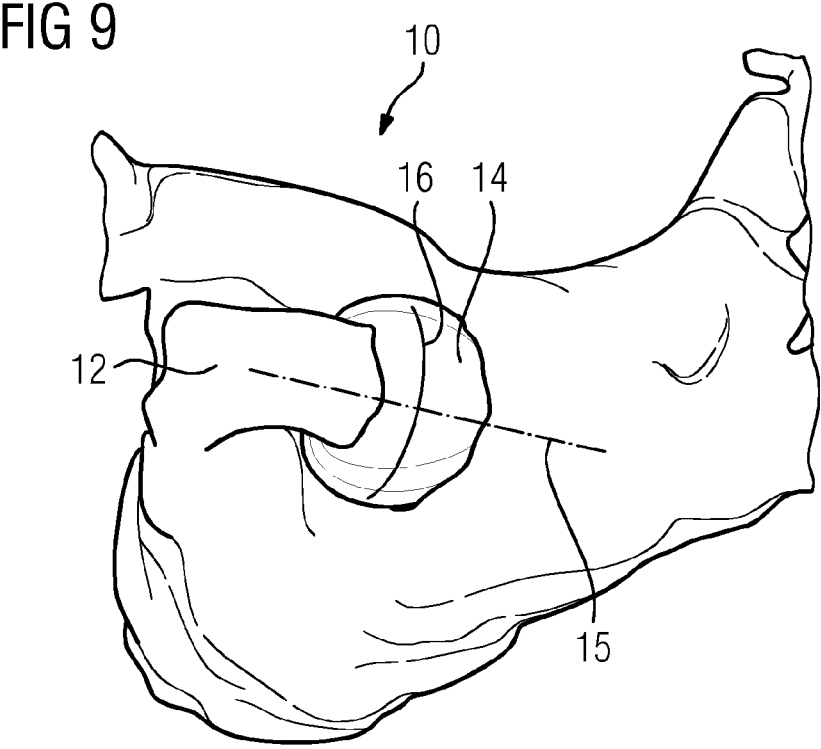
FIG. 9 shows a schematic diagram of a placement of a cryoballoon with an indication of the axis of rotation and of the equator.

FIG. 9 shows a schematic diagram of a placement of the cryoballoon 14 with an indication of the axis of rotation 15 and of the equator 16. Since the cryoballoon 14 is attached to a guide wire and has areas at which the most energy is emitted, it is sensible to assign an appropriate device geometry to it. With the cryoballoon 14, in which most of the energy is emitted along the equator 16, it is obvious to assign an equator plane to the balloon. An axis 15 at right angles to the equator plane which runs through the central point of the balloon makes sense. This corresponds to an axis through the two poles, the pole axis.

Figure 10:
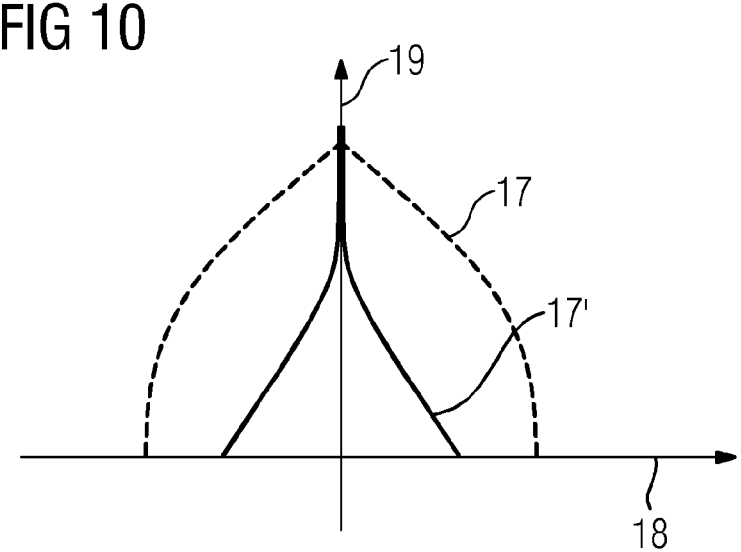
FIG. 10 shows a typical diagram of an energy emission profile.

In FIG. 10 a typical diagram of an energy emission profile 17 is described, showing how the emission of energy 19 changes over distance 18 from a center. In this example of a cryoballoon, the center lies on the equator plane. The associated energy emission value of the energy emission profile 17 is to be read off at the origin of the distance axis 18 and is at its greatest there. It may also be recognized that, as the distance from the center becomes larger, the energy emission value becomes smaller. A second energy emission profile 17' qualitatively has the same properties as the energy emission profile 17, but differs in the maximum energy emission value and the characteristic of the energy emission 19 over the distance 18 from the center.

Figure 11:
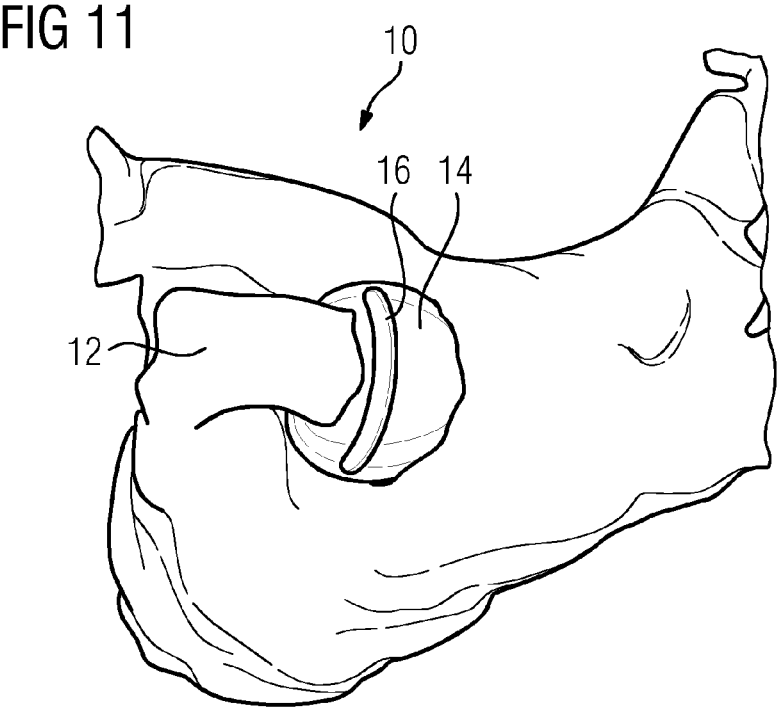
FIG. 11 shows a typical diagram of a visualization of energy emission.

FIG. 11 shows a diagram by way of example of a visualization of energy emission. On the basis of the energy emission profile of the ablation instrument 14, for any point of the ablation instrument and energy emission value to its surroundings, i.e. the surrounding heart 10 or the pulmonary vein 12 may be determined. A color assignment of the energy emission values to a color scale, for example in the form familiar to an observer from a small value in green, via orange to a large value in red, enables the energy emission values to be visualized. In FIG. 11 the indicator 20 shows how most of the energy is emitted to the pulmonary vein 12.

Figure 12:
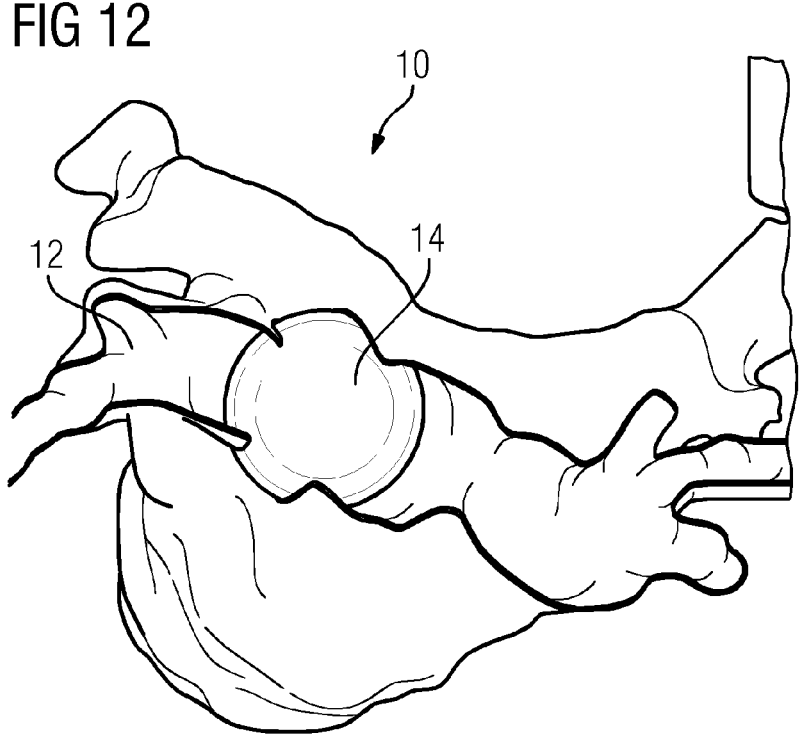
FIG. 12 shows an exemplary embodiment of the result of a placement of a cryoballoon in endoscopic view.

FIG. 12 shows an exemplary embodiment of the results of a placement of a cryoballoon 14 in endoscopic view. In the endoscopic view areas of the heart 10 or of the pulmonary vein 12 and of the placed cryoballoon 14 may be sliced virtually and thereby offer a better insight into the anatomy.

Figure 13:
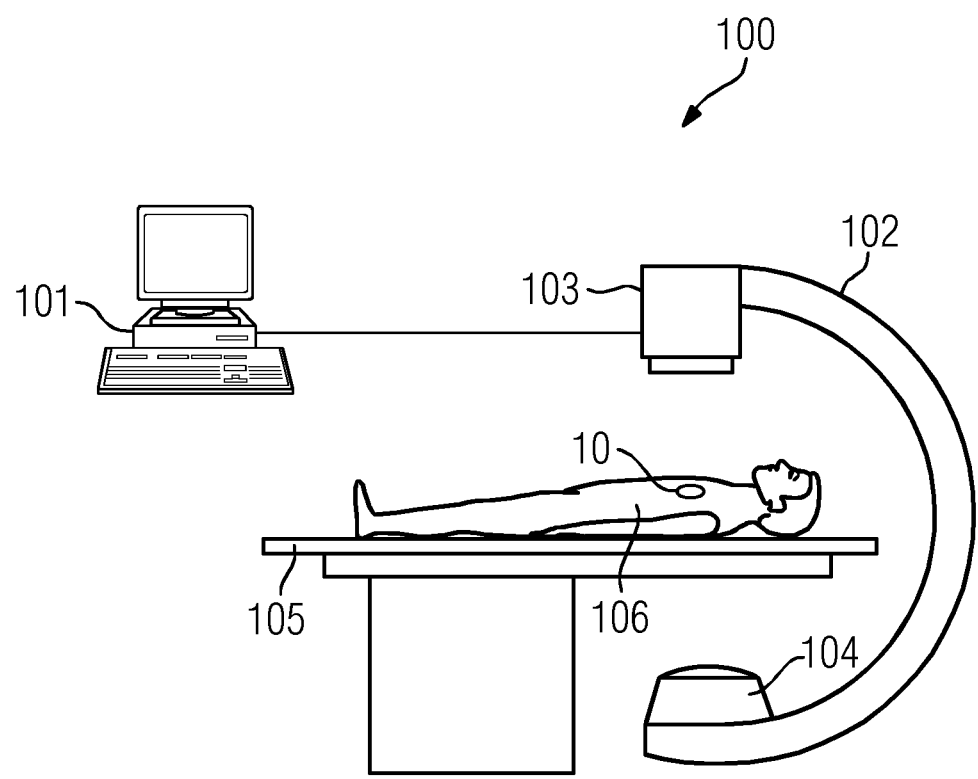
FIG. 13 shows a schematic diagram of an exemplary embodiment of an apparatus for visualizing the quality of an ablation process.

FIG. 13 shows a schematic diagram of an exemplary embodiment of an apparatus 100 for visualizing the quality of an ablation process. The apparatus 100 comprises at least one processing and display means 101, in this exemplary embodiment a computer with the keyboard and monitor. Expediently the processing and display means 101 includes input means not shown in the diagram, such as a computer mouse or a graphics tablet. In this exemplary embodiment, a spatial image is obtained by a C-arm x-ray device which is computed from a suitable series of x-ray images from various directions around the patient. To this end the C-arm x-ray device has a rotatable C-arm 102, on which in an opposing location an x-ray emitter 104 and an x-ray detector 103 are disposed. From the spatial image, e.g. with the aid of a segmentation algorithm, a 3D dataset may be computed, having at least one anatomical object 10, e.g. a heart and lung veins, of an object to be examined 106, here a human patient, who is lying on a patient table 105. The processing and display means 101 is also embodied for carrying out a previously described method, i.e. especially for accepting 3D datasets and position and location information, executing algorithms from mathematics and medical image processing and displaying graphics, e.g. on a monitor.

In summary, the disclosed method and apparatuses are used for individualized virtual planning of ablation therapies, especially with procedures in which it is a matter of placement of single-shot devices. Starting from a 3D model, which shows at least the anatomy but may also contain pointers to functional information, e.g. in connection with scar tissue, the placement of a single-shot device is planned virtually in advance. For example for the treatment of left-side atrial fibrillation different positions of a virtual model of a cryoballoon catheter in a segmented left atrium may be evaluated. Thus it is possible to virtually evaluate the subsequent ablation beforehand and to visualize the resulting wall contact between catheter and tissue. As well as the selection of the appropriate balloon size the balloon positions with optimum wall contact may already be determined. If it transpires during the virtual catheter placement that the cryoballoon is incompatible with the given patient anatomy, primarily a lower-cost RF ablation may be given precedence. It is also possible to compute the resulting energy input. This enables the doctor performing the treatment to better assess the effectiveness of said treatment. To provide the doctor with a good optical illustration of the patient anatomy, the transparency of the 3D model of the left atrium may be changed, as well as an endoscopic view used. A few of the methods shown may also be used for the planning and simulation in the use of RF catheters.

While specific embodiments have been described in detail, those with ordinary skill in the art will appreciate that various modifications and alternative to those details could be developed in light of the overall teachings of the disclosure. For example, elements described in association with different embodiments may be combined. Accordingly, the particular arrangements disclosed are meant to be illustrative only and should not be construed as limiting the scope of the claims or disclosure, which are to be given the full breadth of the appended claims, and any and all equivalents thereof. It should be noted that the term "comprising" does not exclude other elements or steps and the use of articles "a" or "an" does not exclude a plurality.

The invention claimed is:

1. A method of visualizing the quality of an ablation method with a processing and display unit, the method comprising:
   S1) providing a 3D dataset of at least one anatomical object of an object to be examined;
   S2) providing at least one 3D image model of an ablation instrument, wherein the at least one 3D image model models at least a surface of the ablation instrument;
   S3) specifying at least one position and an alignment of the at least one 3D image model of the ablation instrument within the at least one anatomical object;
   S4) incorporating the at least one 3D image model of the ablation instrument into the 3D dataset of the at least one anatomical object at a correct location, wherein the correct location is the specified at least one position and the alignment of the at least one 3D image model of the ablation instrument within the at least one anatomical object;
   S5) displaying at least one part of the incorporated 3D image model of the ablation instrument and of the 3D dataset of the at least one anatomical object;
   S6) determining at least one characteristic quality value as a function of the correct location of the at least one 3D image model of the ablation instrument in relation to the at least one anatomical object,
   wherein an energy emission profile of the ablation instrument is included in the determining of the at least one characteristic quality value, wherein the energy emission profile assigns an energy emission value to each point of the ablation instrument,
   wherein a further characteristic quality value is an overall energy emission value which is defined by sum of all characteristic quality values of energy emission values of the each point of the ablation instrument, and
   wherein an optimization method is provided for determining the at least one position and the alignment of the at least one 3D image model of the ablation instrument within the at least one anatomical object based upon a greatest overall energy emission value.

2. The method as claimed in claim 1, wherein the at least one characteristic quality value is visualized in the displaying of the at least one part of the incorporated 3D image model of the ablation instrument and of the 3D dataset of the at least one anatomical object.

3. The method as claimed in claim 1, wherein, after method step S6), the following method step is executed:
   S7) checking an abort criterion and jumping to the method step S3) if the abort criterion is not fulfilled.

4. The method as claimed in claim 3, wherein the abort criterion comprises activating a pushbutton.

5. The method as claimed in claim 4, wherein the following method steps are executed after method step S6:
   S6a) providing a 2D dataset which represents at least a part of the at least one anatomical object;
   S6b) visualizing in the 2D dataset the at least one position and the alignment of the at least one 3D image model of the ablation instrument and/or visualizing the at least one 3D image model of the ablation instrument, wherein a sectional plane of the at least one 3D image model of the ablation instrument is visualized which corresponds to a projection plane of the 2D dataset; and
   S6c) jumping to step S6a) if a second abort criterion is not fulfilled.

6. The method as claimed in claim 5, wherein the 2D dataset comprises a 2D dataset of a fluoroscopy, and wherein the second abort criterion is the actuation of the pushbutton.

7. The method as claimed in claim 5, wherein, after method step S6a), at least a part of the 3D dataset of the at least one anatomical object is registered with the 2D dataset, wherein an updated position and an updated alignment of the at least one 3D image model of the ablation instrument is determined.

8. The method as claimed in claim 1, wherein the 3D dataset of the at least one anatomical object comprises at least a lung vein and a left atrium of the object to be examined.

9. The method as claimed in claim 1, wherein the 3D dataset of the at least one anatomical object includes information about a position of scar tissue, a wall thickness and/or a wall property.

10. The method as claimed in claim 9, wherein the information is visualized in the displaying of the at least one part of the incorporated 3D image model of the ablation instrument and of the 3D dataset of the at least one anatomical object.

11. The method as claimed in claim 9, wherein the information is included in the determining of the at least one characteristic quality value depending on the correct location of the at least one 3D image model of the ablation instrument relative to the at least one anatomical object.

12. The method as claimed in claim 1,
   wherein the ablation instrument comprises a rotationally-symmetrical object part,
   wherein an axis of rotation of the rotationally-symmetrical object part determines the alignment of the at least one 3D image model of the ablation instrument, and
   wherein a determinable point of the at least one 3D image model of the ablation instrument determines the at least one position of the at least one 3D image model of the ablation instrument.

13. The method as claimed in claim 12, wherein the ablation instrument comprises a balloon-shaped, a pear-shaped or a rim-shaped object part.

14. The method as claimed in claim 12, wherein at least one part of the axis of rotation of the rotationally-symmetrical object part is marked in the at least one 3D image model of the ablation instrument.

15. The method as claimed in claim 1, wherein the at least one characteristic quality value is the energy emission value of the each point of the ablation instrument.

16. The method as claimed in claim 1,
   wherein at least one area is pre-determinable within the at least one anatomical object, and
   wherein, directly after method step S3), a specified position is set to a pre-determinable position or to a closest position within the at least one pre-determinable area when the specified position lies outside the at least one pre-determinable area.

17. An apparatus for visualizing the quality of an ablation process comprising:
   at least one processor and a display unit, the at least one processor:

acquires a 3D dataset of at least one anatomical object of an object to be examined, accepts a 3D image model of an ablation instrument, wherein the 3D image model models at least a surface of the ablation instrument, accepts a position and an alignment of the 3D image model of the ablation instrument within the at least one anatomical object, incorporates the 3D image model of the ablation instrument at a correct location into the 3D dataset of the at least one anatomical object, wherein the correct location is the accepted position and the alignment of the 3D image model of the ablation instrument within the at least one anatomical object, displays, on the display unit, at least a part of the incorporated 3D image model of the ablation instrument and of the 3D dataset of the at least one anatomical object, and determines at least one characteristic quality value depending on the correct location of the 3D image model of the ablation instrument relative to the at least one anatomical object, wherein an energy emission profile of the ablation instrument is included in the determining of the at least one characteristic quality value, wherein the energy emission profile assigns an energy emission value to each point of the ablation instrument, wherein a further characteristic quality value is an overall energy emission value which is defined by sum of all characteristic quality values of energy emission values of the each point of the ablation instrument, and wherein an optimization method is provided for determining the position and the alignment of the 3D image model of the ablation instrument within the at least one anatomical object based upon a greatest overall energy emission value.

\* \* \* \* \*